(12) United States Patent
Rozas et al.

(10) Patent No.: US 10,398,405 B2
(45) Date of Patent: Sep. 3, 2019

(54) GAIN CALIBRATION AND CORRECTION IN RADIATION SYSTEM

(71) Applicant: Analogic Corporation, Peabody, MA (US)

(72) Inventors: David Rozas, Brighton, MA (US); Aleksander Roshi, Medford, MA (US); Charles H. Shaughnessy, Hamilton, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 16/235,409

(22) Filed: Dec. 28, 2018

(65) Prior Publication Data

US 2019/0192106 A1    Jun. 27, 2019

Related U.S. Application Data

(62) Division of application No. 14/771,858, filed as application No. PCT/US2013/028624 on Mar. 1, 2013, now Pat. No. 10,206,650.

(51) Int. Cl.
*A61B 6/04* (2006.01)
*A61B 6/00* (2006.01)
(Continued)

(52) U.S. Cl.
CPC .............. *A61B 6/585* (2013.01); *A61B 6/032* (2013.01); *G06T 11/005* (2013.01); *H01J 35/106* (2013.01); *A61B 6/5252* (2013.01); *H01J 2235/1204* (2013.01); *H01J 2235/1266* (2013.01)

(58) Field of Classification Search
None
See application file for complete search history.

(56) References Cited

U.S. PATENT DOCUMENTS 5,949,842 A    9/1999   Schafer et al.
8,081,733 B2  12/2011  Basu et al.
(Continued)

FOREIGN PATENT DOCUMENTS

WO    2003/028554 A1    4/2003

OTHER PUBLICATIONS

Written Opinion of the International Searching Authority for PCT Application No. PCT/US2013/028624, 6 pages, dated Nov. 6, 2013.
(Continued)

*Primary Examiner* — Thomas R Artman
(74) *Attorney, Agent, or Firm* — TraskBritt

(57) ABSTRACT

Among other things, one or more techniques and/or systems for calibration of a radiation system to compute a gain correction(s) are provided. A calibration procedure is performed during which a portion of the detector array is shadowed by an object, causing the detector array to be non-uniformly exposed to radiation. A portion of a projection generated from the calibration procedure and indicative of radiation that did not traverse the object is separated from a portion of the projection indicative of radiation that did traverse the object, and a gain correction(s) is computed from the portion of the projection indicative of radiation that did not traverse the object (e.g., and is thus indicative of radiation that merely traversed air).

12 Claims, 7 Drawing Sheets

(51) Int. Cl.
*H01J 35/10* (2006.01)
*G06T 11/00* (2006.01)
*A61B 6/03* (2006.01)

(56) References Cited

U.S. PATENT DOCUMENTS

| | | | |
|---|---|---|---|
| 8,121,250 B2* | 2/2012 | Dafni | A61B 6/032 |
| | | | 378/18 |
| 8,611,627 B2* | 12/2013 | Wu | A61B 6/032 |
| | | | 382/131 |
| 9,198,632 B2 | 12/2015 | Zhang et al. | |
| 9,299,171 B2 | 3/2016 | Bredno et al. | |
| 9,636,079 B2* | 5/2017 | Bredno | A61B 6/582 |
| 2010/0195804 A1* | 8/2010 | Dafni | A61B 6/032 |
| | | | 378/207 |
| 2010/0215143 A1 | 8/2010 | Basu et al. | |
| 2011/0176663 A1 | 7/2011 | Shaughnessy | |
| 2011/0249879 A1* | 10/2011 | Wu | A61B 6/032 |
| | | | 382/131 |
| 2014/0014828 A1 | 1/2014 | Bredno et al. | |
| 2014/0241489 A1 | 8/2014 | Zhang et al. | |
| 2015/0103972 A1* | 4/2015 | Bredno | A61B 6/582 |
| | | | 378/7 |
| 2016/0015357 A1 | 1/2016 | Rozas et al. | |

OTHER PUBLICATIONS

International Search Report cited in related application No. PCT/US2013/028624 dated Nov. 6, 2013, pp. 10.

* cited by examiner

GAIN CALIBRATION AND CORRECTION IN RADIATION SYSTEM

CROSS-REFERENCE TO RELATED APPLICATIONS

This application is a divisional of U.S. patent application Ser. No. 14/771,858, filed Sep. 1, 2015, which is a national phase entry under 35 U.S.C. § 371 of International Patent Application PCT/US2013/28624, filed Mar. 1, 2013, designating the United States of America and published in English as International Patent Publication WO 2014/133544 A1 on Sep. 4, 2014.

BACKGROUND

The disclosure relates to the field of radiation scanning and/or radiation imaging. It finds particular application with computed-tomography (CT) scanners where one or more calibration tables are utilized to correct measurements acquired during an examination of a subject (e.g., person, luggage, etc.). It also relates to other radiation systems where it is desirable to correct measurements acquired during an examination to account for errors due to, among other things, manufacturing defects, electronic noise, and/or degradation of a detector array configured to acquire the measurements, for example.

Radiation systems (e.g., also referred to as imaging systems, radiation imaging systems, radiation scanning systems, and/or the like) such as computed tomography (CT) systems, diffraction CT, single-photon emission computed tomography (SPECT) systems, projection systems, and/or line systems, for example, are used to provide information pertaining to interior aspects of a subject. Generally, the subject is exposed to radiation comprising photons (e.g., such as x-ray photons, gamma ray photons, etc.) to measure attenuation by the subject (e.g., which may be indicative of the density of the subject and/or aspects thereof). In some embodiments, an image(s) is formed based upon the radiation absorbed and/or attenuated by interior aspects of the subject, or rather an amount of photons that is able to pass through the subject. Generally, highly dense aspects of a subject absorb and/or attenuate more radiation than less dense aspects, and thus an aspect having a higher density, such as a bone or metal, for example, may be apparent when surrounded by less dense aspects, such as muscle or clothing.

To reconstruct an image from measurements acquired during the examination and/or to perform other processes using the measurements (e.g., such as automated threat analysis processes), it is desirable for the measurements to accurately reflect the amount of radiation detected and to reduce (e.g., to a minimum) errors in the measurements (e.g., caused by manufacturing defects in the detector array material and/or readout electronics, degradation of the detector array material and/or readout electronics over time, etc.). Accordingly, a set of calibration procedures may be periodically or intermittently performed to compute correction factors that adjust the measurements acquired from the detector array to correct for the errors (e.g., to reduce the contribution of the errors to the overall measurements). For example, a set of one or more calibration procedures may be performed daily, weekly, and/or at other scheduled times to compute such correction factors.

One such calibration procedure that is commonly performed is an air scan. During an air scan, the detector array is substantially uniformly exposed to radiation. Typically, this is achieved by removing objects, such as a gurney for supporting subjects under examination, from a field of view to provide a clear line-of-sight from a radiation source to the detector array (e.g., such that radiation experiences little to no attenuation during the air scan). Accordingly, differences in measurements between detector cells of the detector array may be attributed to error, and a gain correction for respective detector cells may be identified that corrects the measurements from the corresponding detector cell (e.g., to reduce differences in the measurements between detector cells when an air scan is performed). The gain corrections are typically stored in an air table, also referred to as an air calibration table, and applied to measurements acquired during an examination of a subject to correct the measurements (e.g., such that variations in the corrected measurements reflect variations due to attenuation by the subject, and not due to errors).

BRIEF SUMMARY

Aspects of the disclosure address the above matters, and others. According to one aspect, a method of calibrating a computed tomography (CT) system when a field of view is partially obstructed by an object is provided. The method comprises acquiring a projection from a calibration procedure performed while the field of view was partially obstructed by the object, the projection comprising object projection data indicative of radiation that traversed the object and calibration projection data indicative of radiation that did not traverse the object. The method also comprises separating the calibration projection data from the object projection data and computing one or more gain corrections as a function of the calibration projection data. The one or more gain corrections are utilized during an examination procedure to correct measurements yielded from a detector array of the CT system.

According to another aspect, a system for calibrating a computed tomography (CT) system is provided. The system comprises a gain computation component configured to compute one or more gain corrections to apply to measurements yielded from an examination of a subject. The one or more gain corrections are computed from a projection yielded from a calibration procedure performed while a detector array of the CT system was partially shadowed by an object such that the detector array was non-uniformly exposed to radiation.

According to yet another aspect, a method for calibrating a computed tomography (CT) system is provided. The method comprises preforming a calibration procedure on the CT system. The calibration procedure comprises non-uniformly exposing a detector array of the CT system with radiation to generate one or more projections. The method also comprises computing one or more gain corrections as a function of at least some of the one or more projections. The one or more gain corrections are configured to correct measurements yielded from an examination of a subject.

Those of ordinary skill in the art may appreciate still other aspects of the disclosure upon reading and understanding the appended description.

BRIEF DESCRIPTION OF THE DRAWINGS

The disclosure is illustrated by way of example and not limitation in the figures of the accompanying drawings, in which like references generally indicate like elements and in which.

DETAILED DESCRIPTION

Figure 1:
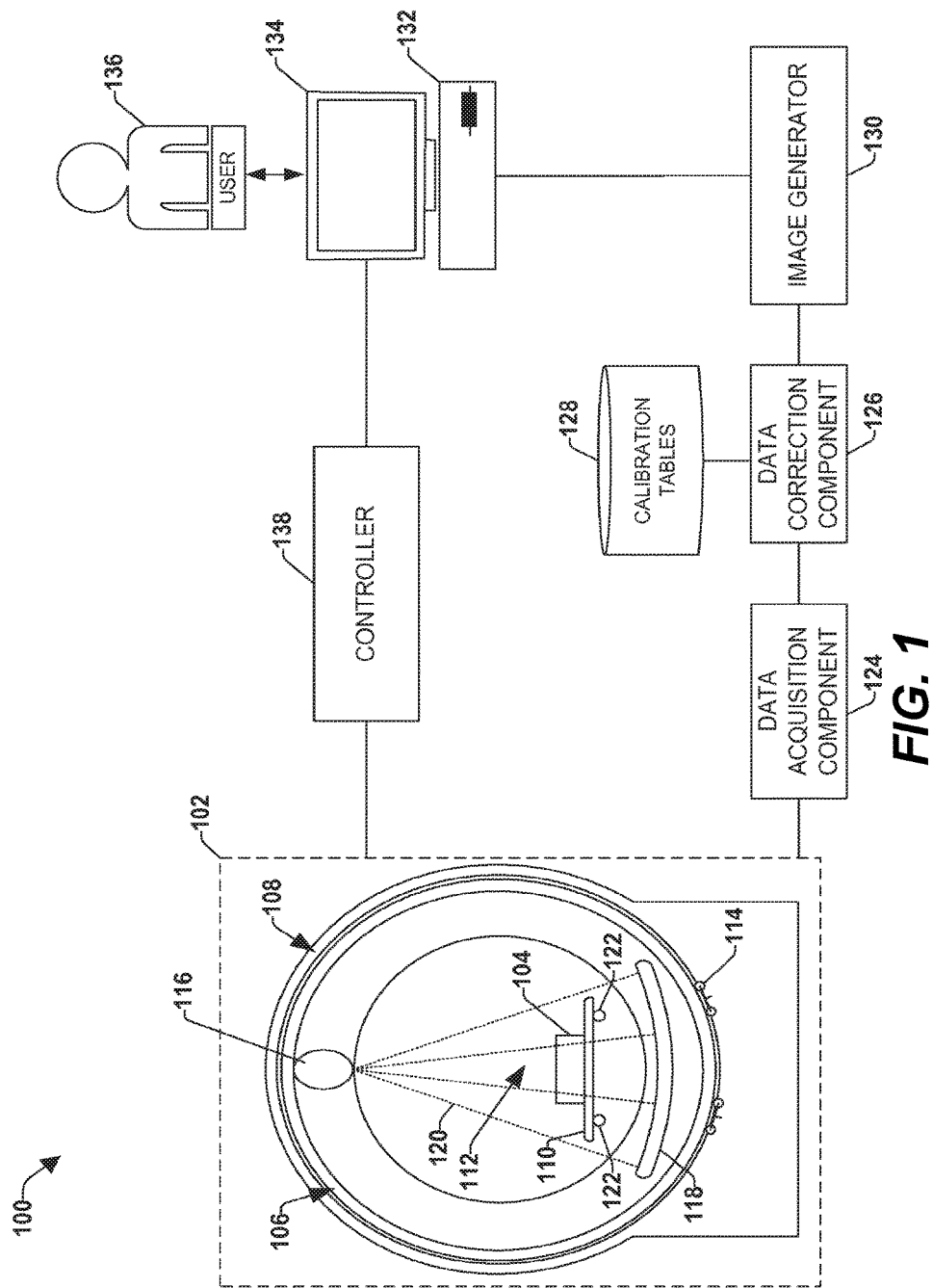
FIG. 1 is a schematic block diagram illustrating an example environment where a radiation system such as described herein may be implemented.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

While an air scan calibration procedure is useful for identifying errors and/or for addressing errors in measurements acquired from a detector array, in some applications it may not be possible to remove objects from a field of view and/or to expose the detector array to a substantially uniform amount of radiation. For example, in some embodiments, it may be difficult and/or time consuming to remove support rails for a gurney or other subject support from the field of view. Accordingly, respective detector cells of a first portion of the detector array (e.g., not shadowed by objects) may measure a first amount of radiation and respective detector cells of a second portion of the detector array (e.g., shadowed by objects) may measure a second amount of radiation. Thus, exposing the detector array to a substantially uniform amount of radiation during a calibration procedure may be difficult.

Accordingly, one or more systems and/or techniques are provided herein to compute a gain correction using a calibration procedure performed while a field of view is partially obstructed by an object. That is, stated differently, systems and/or techniques are provided herein to compute one or more gain corrections from a calibration procedure where a field of view is partially obstructed by an object (e.g., and a portion of a detector array is shadowed), causing a detector array of the radiation system to be exposed to a non-uniform amount of radiation.

A gain correction is computed for a corresponding correction unit, where the size/scope of a correction unit may be application specific and/or user-specified. For example, in some embodiments, one gain correction is computed for respective detector cells of a detector array. Accordingly, a first gain correction is computed to correct measurements yielded from a first detector cell, a second gain correction is computed to correct measurements yielded from a second detector cell, etc. In such embodiments, a correction unit may be defined as all measurements yielded from a single detector cell. In other embodiments, it may be desirable to compute a gain correction for a group of detector cells. In such embodiments, the correction unit may be defined as all measurements yielded from the group of detector cells. In still other embodiments multiple gain corrections may be computed for a single detector cell. For example, a first gain correction may be computed to apply to measurements yielded from a first detector cell during a first portion of a rotation and a second gain correction may be computed to apply to measurements yielded from the first detector cell during a second portion of a rotation. Accordingly, in such an embodiment, the correction unit may be defined as all measurements yielded from a detector cell during a specified portion of a rotation.

Moreover, object, objects, and/or the like are intended to refer to items of a radiation system and subject, subjects, and/or the like are intended to refer to items configured to be examined by the radiation system. For example, an object may refer to a support article, support rails for supporting the support article, etc. A subject may refer to a patient, baggage, lumber, etc., that is intended to be examined/scanned by the radiation system.

The gain correction(s) are computed by separating a portion of the projection data not representative of the object (e.g., and instead representative of radiation having a substantially clear line-of sight between a radiation source and the detector array) from a portion of the projection data representative of the object (e.g., and thus representative of radiation not having a clear line-of-sight between the radiation source and the detector array due to the position of the object between the radiation source and the detector array). The portion of a projection (or set of projections) not representative of the object may be referred to as calibration projection data because such data is indicative of (e.g., represents measurements of) radiation that did not traverse the object. The portion of a projection (or set of projections) representative of the object may be referred to as object projection data because such data is indicative of (e.g., represents measurements of) radiation that traversed the object. Thus, a projection (or set of projections) comprises calibration projection data and object projection data. Using the calibration projection data (e.g., and not the object projection data), one or more gain corrections can be computed and stored in an air table to be used for correcting measurements yielded from a detector array during a non-calibration procedure, for example.

In some embodiments, a plurality of projections is acquired during the calibration procedure and is utilized to compute the gain correction(s). For example, a first set of projections may be acquired that is indicative of the object being located at a first position relative to an axis of rotation for the radiation source and/or detector array and a second set of projections may be acquired that is indicative of the object being located at a second position relative to the axis of rotation. Accordingly, the object may be repositioned between when measurements represented in the first set of projections are acquired and when measurements represented in the second set of projections are acquired. The first set of projections and the second set of projections may be subsequently combined to generate a combined set of projections and the combined set of projections may be utilized to compute the gain correction(s), for example. As will be appreciated, a projection generally corresponds to a particular view angle, and thus a set of projections may comprise one or more projections corresponding to different view angles. For example, a set of projections may comprise 360 projections for a 360 degree rotation of a CT system. When views correspond to less than 1 degree, for example, a set of projections for a 360 degree rotation may comprise more than 360 projections. For example, a 360 degree rotation may have 960 views or projections when a view corresponds to less than 1 degree.

It may be appreciated that while the calibration projection data is indicative of (e.g., represents measurements of) radiation that did not traverse the object, and is thus similar to data generated by an air scan, the radiation may experience at least some attenuation. For example, in some embodiments, a radiation system may comprise a cover that overlays a window through which radiation is emitted (e.g., to mitigate dust particles and/or other particles from contacting the radiation source). Such a cover typically attenuates little to no radiation (e.g., the cover is substantially radiation transparent). Moreover, radiation that is attenuated by the cover is typically attenuated substantially uniformly. Accordingly, if no objects were positioned within the field of view, the detector array would be exposed to a substantially uniform amount of radiation even if the field of view is obstructed by the cover.

It may also be appreciated that while the applicability of such systems and/or techniques are described with particular reference to computed tomography (CT) systems, such systems and/or techniques may also find applicability to other radiation systems (e.g., ionizing radiation systems) where a calibration procedure to correct for errors in measurements generated by a detector array would be useful.

FIG. 1 illustrates an example environment 100 of a radiation system as provided for herein. It may be appreciated that the example environment 100 merely provides an example arrangement and is not intended to be interpreted in a limiting manner, such as necessarily specifying the location, inclusion, and/or relative position of the components depicted therein. By way of example, the data acquisition component 124 may be part of the detector array 118. Moreover, the instant application is not intended to be limited to use with a particular radiation measurement technique and/or a particular type of radiation system. For example, the systems and/or techniques described herein may find applicability to charge-integrating radiation systems, photon counting radiation systems, single-energy radiation systems, multi-energy (dual-energy) radiation systems, indirect conversion radiation systems, and/or direct conversion radiation systems, for example.

In the example environment 100, an examination unit 102 of the radiation system is configured to examine subjects (e.g., bags, suitcases, patients, etc.), such as a first subject 104. By way of example, the examination unit 102 may be configured to examine a series of bags placed on a conveyor belt and conveyed through the radiation system and/or may be configured to examine patients placed onto a gurney and positioned within an examination region 112 of the examination unit 102.

The examination unit 102 can comprise a rotating gantry 106 and a (stationary) support structure 108 (e.g., which may encase and/or surround at least a portion of the rotating gantry 106 (e.g., as illustrated with an outer, stationary ring, surrounding an outside edge of an inner, rotating ring)). Subjects, such as the first subject 104, can be placed on a support article 110 of the examination unit 102, such as a gurney or conveyor belt, and conveyed or translated into the examination region 112 (e.g., a hollow bore in the rotating gantry 106) configured to selectively receive subjects. The rotating gantry 106 can be rotated about the subject(s) during the examination and/or moved relative to the subject(s) by a rotator 114, such as a motor, drive shaft, chain, roller truck, etc. An axis about which the rotating gantry, radiation source, and/or detector array are rotated is referred to as an axis of rotation and conventionally has been defined as an axis extending in a z-direction (e.g., into and out of the page). Accordingly, a plane in which the rotating gantry, detector array, and/or radiation source rotate is typically defined as an x, y plane.

By way of example, in a radiation system configured for medical applications, the examination unit 102 can comprise a gurney configured to translate patients into and/or within the examination region 112 (e.g., in a direction substantially parallel to the axis of rotation). The gurney can be supported by one or more support rails 122 that extend into and/or through the examination region 112 and are configured to support the weight of the gurney and/or a patient undergoing examination. In this way, in some embodiments, the gurney is not cantilevered during an examination of a patient and/or an extent to which the gurney is cantilevered is reduced relative to a radiation system where there are no support rails 122 that extend into the examination region 112.

As used herein, the examination region 112 of the examination unit 102 is intended to refer to a region of the examination unit 102 through which radiation 120 traverses and may define a field of view for the examination unit 102. Accordingly, to examine a subject during an examination procedure, the subject or an aspect thereof to be examined is positioned within the examination region 112 (e.g., positioned within a field of view) and exposed to radiation 120.

The rotating gantry 106 may surround a portion of the examination region 112 and may comprise a radiation source 116 (e.g., an ionizing radiation source such as an x-ray source or gamma-ray source) and a detector array 118 that is mounted on a substantially diametrically opposite side of the rotating gantry 106 relative to the radiation source 116. In this way, the relative position of the radiation source 116 and the detector array 118 (e.g., the position of the radiation source(s) 116 relative to the detector array 118) may be maintained during an examination of the subject(s), for example.

During the examination of a subject, such as the first subject 104, the radiation source 116 emits fan, cone, wedge, and/or other shaped radiation 120 configurations from a focal spot(s) of the radiation source 116 (e.g., a region within the radiation source 116 from which radiation 120 emanates) into the examination region 112. It may be appreciated that such radiation 120 may be emitted substantially continuously and/or may be emitted intermittently or periodically (e.g., a brief pulse of radiation 120 is emitted followed by a resting period during which the radiation source 116 is not activated). Moreover, the radiation 120 may be emitted at a single energy spectrum or may be emitted at two or more different energy spectra. Also, a focal spot of the radiation source 116, through which radiation is emitted, may be substantially stationary and/or may move (e.g., creating a flying focal spot).

As the emitted radiation 120 traverses the subject 104, the radiation 120 may be attenuated differently by different aspects of the subject 104. Because different aspects attenuate different percentages of the radiation 120, an image(s) of the subject 104 may be generated based upon the attenuation, or variations in the number of photons that are detected by the detector array 118, or rather by detector cells of the detector array 118. For example, more dense aspects of the subject 104, such as a bone or metal plate, may attenuate more of the radiation 120 (e.g., causing fewer photons to strike the detector array 118) than less dense aspects, such as skin or clothing.

Radiation detected by the detector array 118 may be directly converted and/or indirectly converted into analog signals that can be transmitted from the detector array 118 to a data acquisition component 124 operably coupled to the detector array 118. The analog signal(s) may carry information indicative of the radiation detected by the detector array 118 (e.g., such as an amount of charge measured over a sampling period, an energy level of detected radiation, etc.), and the data acquisition component 124 may be configured to convert the analog signals into digital signals and/or to compile signals that were transmitted within a predetermined time interval, or measurement interval, using various techniques (e.g., integration, photon counting, etc.). The compiled signals are typically in projection space and are, at times, referred to as projections. A projection may be representative of the information collected or measurements acquired by respective detector cells of the detector array 118 during a particular interval of time or view. Moreover, a set of projections may be compiled to represent measurements acquired over a plurality of views. For example, a first set of projections may be representative of the information collected or measurements acquired during a first 360 degree rotation of the rotating gantry 106 and a second set of projections may be representative of information collected or measurements acquired during a second 360 degree rotation. In some embodiments, there may be a break between the first 360 degree rotation and the second 360 degree rotation (e.g., to facilitate moving an object within the examination region 112). In other embodiments, the rotating gantry 106 may rotate substantially continuously to acquire the first set of projections and the second set of projections.

During an examination of a subject, at least a portion of the projections acquired from the examination are typically representative of the subject. Although, due to the size of the subject and/or position of the subject relative to the detector array 118, portions of one or more projections may not be representative of the subject (e.g., and instead may be representative of air and/or another subject). During a calibration procedure, such as performed to determine a gain correction(s), no subject is typically examined. Accordingly, a projection and/or set of projections yielded from the calibration procedure is indicative of air and/or objects that are not removed from the examination region 112 for the calibration procedure.

Where one or more objects are not removed for the calibration procedure, such as support rails 122, at least a first portion of one or more projections acquired during the calibration procedure may be representative of radiation 120 that did not traverse the object(s) (e.g., radiation 120 that followed a substantially object-free path from the radiation source 116 to the detector array 118) and at least a second portion of one or more projections may be representative of radiation 120 that traversed the object (e.g., and thus followed a path from the radiation source 116 to the detector array 118 that intersected the object(s)). A portion or portions of one or more projections indicative of or representative of radiation that did not traverse the object(s) may be referred to as calibration projection data, and a portion or portions of one or more projections indicative of or representative of radiation that traversed the object(s) may be referred to as object projection data.

The example environment 100 further comprises a data correction component 126 configured to compute one or more gain corrections, from a projection and/or set of projections acquired from a calibration procedure and to correct a projection and/or set of projections yielded from an examination of a subject(s) by applying the one or more gain corrections to the projection(s) yielded from the examination procedure (e.g., to reduce the effect of errors on the projection(s)). Stated differently, the data correction component 126 is configured to compute/update correction factors, such as a gain correction(s) based upon calibration procedures that are performed periodically or intermittently (e.g., daily). The data correction component 126 is further configured to apply the computed/updated gain corrections to a projection(s) acquired during an examination procedure to correct the values of measurements represented in the projection(s).

As may be described in more detail below, the calibration procedure is performed while one or more objects, such as the support rails 122 for supporting the support article 110, are present in the examination region 112 and partially obstruct a field of view. That is, the calibration procedure is performed while a portion of the detector array 118 is shadowed or masked by the one or more objects. Accordingly, during the calibration procedure, the detector array 118 is non-uniformly exposed to radiation. Thus, at least a portion of a projection(s) acquired from the calibration procedure comprises object projection data and at least a portion of the projection(s) comprises calibration projection data (e.g., due to the object merely shadowing a portion of the detector array 118 and not the entire detector array 118.

The one or more a gain corrections, are computed as a function of the calibration projection data. Accordingly, as a preliminary action, the data correction component 126 may be configured to separate the calibration projection data from the object projection data using analytic, iterative, or other techniques that are configured to determine the probability that respective measurements of the projection are indicative of an object (e.g., and thus categorized as object projection data) or not indicative of an object (e.g., and thus categorized as calibration projection data). Example techniques for identifying the calibration projection data in the projection(s) and/or for separating the calibration projection data from the object projection data may be further detailed below with respect to FIG. 3, for example.

After the calibration projection data has been separated from the object projection data, the data correction component 126 may proceed to compute one or more gain corrections using the calibration projection data. In one embodiment, the data correction component 126 may be configured to compute a gain correction or a corresponding measurement unit. Gain corrections computed by the data correction component 126 may be stored in a data storage unit 128. In one embodiment, the gain corrections are arranged in a table, such as an air calibration table or other calibration table, and stored in the data storage unit 128. In this way, the gain corrections are arranged in a manner that provides for easy retrieval and/or application to projections yielded from an examination procedure.

During an examination of a subject(s), the data correction component 126 is configured to retrieve the gain corrections from the data storage unit 128 and apply the gain corrections to a projection(s) yielded from an examination procedure. In this way, measurements acquired from one or more detector cells of the detector array 118 during the examination procedure are corrected (e.g., adjusted) to account for errors inherent in the radiation system (e.g., such as due to manufacturing defects, degradation of the detector array 118 over time, etc.). Accordingly, corrected projection(s) representative of the subject may be generated by the data correction component 126, for example.

In the example environment 100, an image generator 130 (e.g., or image reconstructor) is configured to receive the corrected projection(s) that is output by the data correction component 126. Such an image generator 130 may be configured to generate one or more images of a subject represented by the corrected projection(s), such as the first subject 104, from the corrected projection(s) using a suitable analytical, iterative, and/or other image generation technique (e.g., backprojection reconstruction, tomosynthesis reconstruction, iterative reconstruction, etc.). In this way, the data is converted from projection space to image space, a domain that may be more understandable by a user 136 viewing the image(s), for example.

It may be appreciated that where the position of the radiation source 116 and/or the detector array 118 change relative to a subject, such as the first subject 104, during the examination (e.g., due to the rotation of the radiation source 116 and/or detector array 118 about the subject 104), volumetric data indicative of the subject 104 may be yielded from the information generated by the detector array 118. Accordingly, the image(s) generated by the image generator 130 may be three-dimensional images (e.g., also referred to as volumetric images), for example. Further, in one embodiment, the image generator 130 may be configured to project the volumetric images to generate two-dimensional images.

The example environment 100 further comprises a terminal 132, or workstation (e.g., a computer), that may be configured to receive images generated by the image generator 130. At least some of the received images may be provided by the terminal 132 for display on a monitor 134 to a user 136 (e.g., security personnel, medical personnel, etc.). In this way, the user 136 can inspect the image(s) to identify areas of interest within subject(s) undergoing examination, such as the first subject 104, for example. The terminal 132 can also be configured to receive user input which can direct operations of the examination unit 102 (e.g., a speed to rotate, a speed and direction of a support article 110, etc.), for example.

In the example environment 100, a controller 138 is operably coupled to the terminal 132. The controller 138 may be configured to control operations of the examination unit 102, for example. By way of example, in one embodiment, the controller 138 may be configured to receive information from the terminal 132 and to issue instructions to the examination unit 102 indicative of the received information (e.g., adjust a speed of a conveyor belt).

Figure 2:
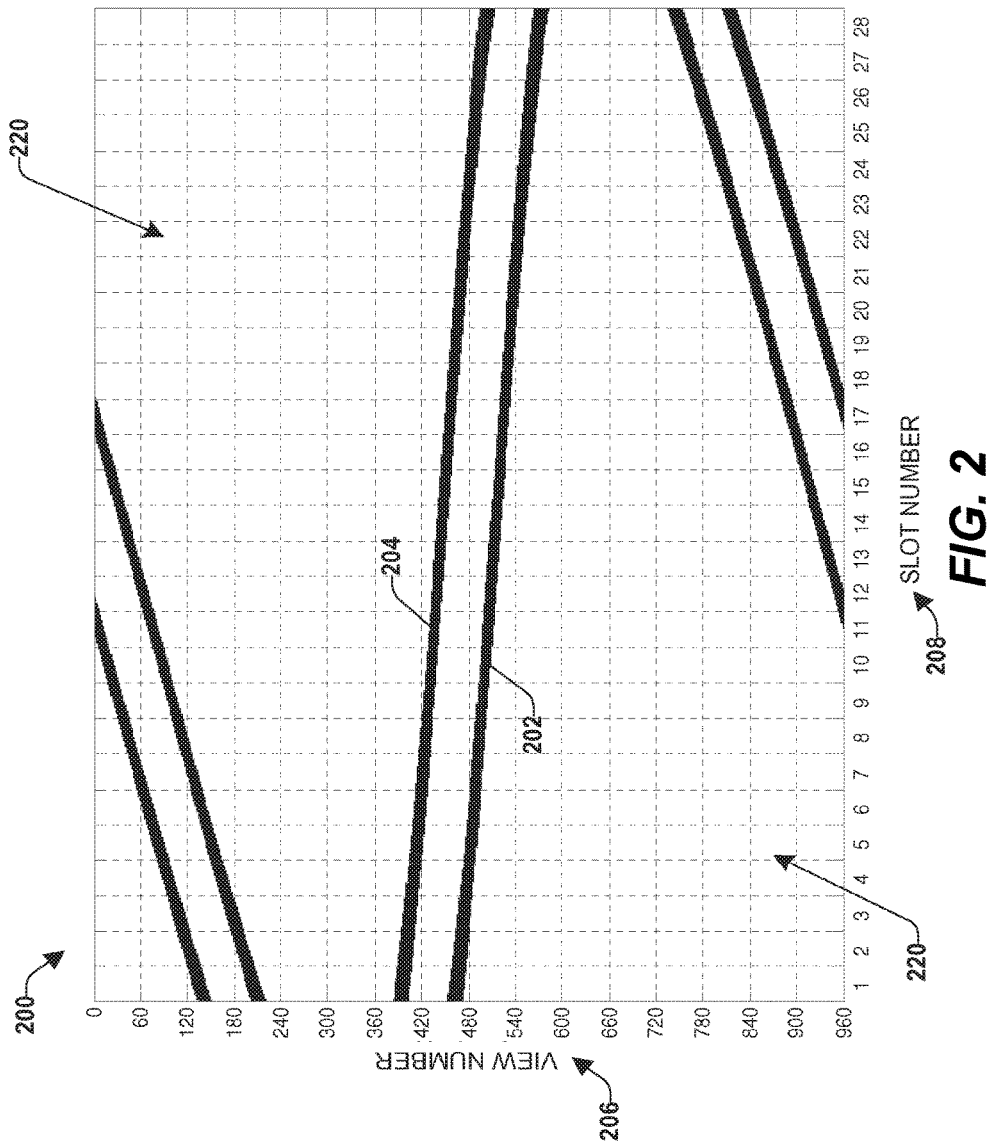
FIG. 2 illustrates an example projection set yielded from a calibration procedure.

FIG. 2 illustrates an example projection set 200 that may be acquired by a data correction component (e.g., 126 in FIG. 1) from a calibration procedure performed while a field of view is partially obstructed by an object(s) (e.g., causing a detector array to be partially shadowed by the object(s) during a range of views represented by the projection set 200).

A first sinusoid 202 of the projection set 200 is representative of a first object that is shadowing the detector array and a second sinusoid 204 of the projection set 200 is representative of a second object that is shadowing the detector array. For example, the first object may be a first metal support rail (e.g., 122 in FIG. 1) and the second object may be a second metal support rail (e.g., 122 in FIG. 1), respectively positioned within an examination region (e.g., 112 in FIG. 1) of the radiation system during the calibration procedure.

Where a rotating gantry, detector array, and/or radiation source are configured to rotate about an axis of rotation, the CT system may acquire information from a plurality of views. The y-axis 206 of the projection set 200 represents a view number in which measurements were acquired. By way of example, where the rotating gantry is configured to rotate by 360 degrees relative to or about the axis of rotation and/or relative to an object(s) shadowing the detector array, the 360 degree rotation may be dissected into 960 views, where respective views represent measurements acquired during a fraction of a rotational degree. It may be appreciated that if a horizontal line were drawn on the projection set 200, the horizontal line would intersect measurements acquired while the rotating gantry was at a fixed location (e.g., particular angular view) relative to the axis of rotation and/or relative to the object(s).

The x-axis 208 of the projection set 200 represents the detector cell which acquired the measurement. That is, respective detector cells may be (sequentially) assigned a number and arranged along the x-axis by detector cell number. In the illustrated embodiment, the detector cells are grouped into what are referred to as slots (e.g., to avoid listing respective detector cells on the x-axis). By way of example, for the projection set 200, the detector cells are grouped into 28 slots, where respective slots may represent measurements yielded from 10 or more detector cells, for example. It may be appreciated that if a vertical line were drawn on the projection set 200, the vertical line would be a locus of measurements acquired from a single detector cell (e.g., at 960 different view angles during a 360 degree rotation).

The darker, sinusoidal portions 202, 204 of the projection set 200 are indicative of radiation that traversed the object) (e.g., the metal support rails) and may be referred to as object projection data. The lighter (e.g., white) portions 220 of the projection set 200 are indicative of radiation that did not traverse the objects and may be referred to as air or gain calibration projection data.

Figure 3:
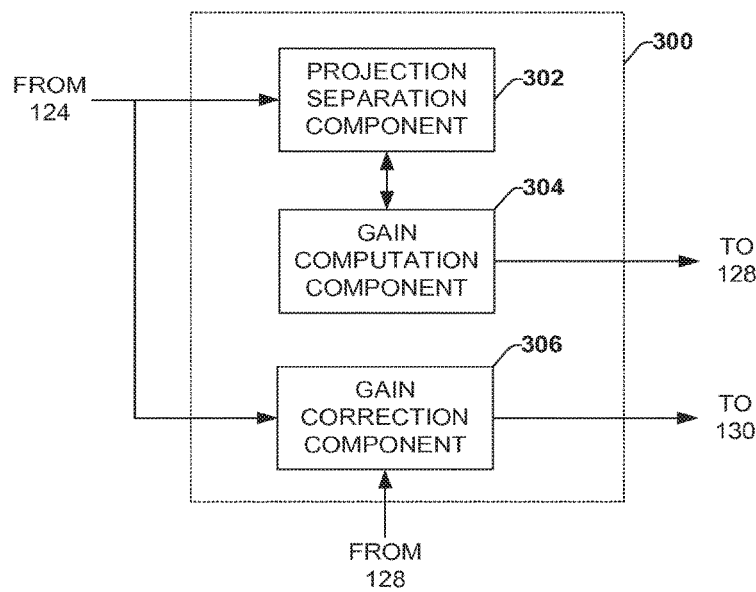
FIG. 3 is a schematic block diagram illustrating an example data correction component.

FIG. 3 illustrates an example arrangement for components of a projection set 200, such as the data correction component 126 of FIG. 1. The example data correction component 300 is primarily configured to perform two roles. The first role is to determine a gain correction(s) based upon a projection (e.g., 200 in FIG. 2) obtained from a calibration procedure performed while a portion of a detector was shadowed by an object(s) (e.g., and thus a field of view was partially obstructed by the object(s)). The second role is to apply the gain correction(s) to a projection(s) obtained from an examination procedure.

To determine or compute one or more gain corrections, the data correction component 300 comprises a projection separation component 302 and a gain computation component 304.

The projection separation component 302 is configured to separate calibration projection data from object projection data of a projection and/or projection set using an analytic, iterative, and/or other data identification and/or separation technique. By way of example, in some embodiments, the projection and/or set of projections is indicative of a plurality of measurements, and the projection separation component 302 is configured to determine an average intensity of the measurements. Respective measurements of the plurality of measurements may be compared to the average intensity to identify calibration projection data and/or object projection data. For example, the projection separation component 302 may be configured to label data associated with measurements indicative of an intensity that deviates from the average intensity by less than a specified threshold as calibration projection data and to label data associated with measurements indicative of an intensity that deviates from the average intensity by more than or equal to a specified threshold as object projection data.

In other embodiments, the projection separation component 302 is configured to compare measurements of a projection and/or set of projections to a (e.g., user-specified) expected intensity. For example, in some embodiments, an expected intensity value is specified for the detector array, or for a group of cells, and the projection separation component 302 is configured to compare the expected intensity value to actual intensity measurements of the projection and/or set of projections. Intensity measurements that deviate from the expected intensity value by more than a specified threshold may be identified as object projection data, and intensity measurements that deviate from the expected intensity value by less than a specified threshold may be identified as calibration projection data.

In another embodiment, a baseline calibration procedure is performed during which a field of view is substantial clear (e.g., there are no objects in the field of view) to derive a baseline set of intensity values, and the projection separation component 302 may be configured to compare intensity measurements acquired during a subsequent calibration procedure to a corresponding intensity value of the baseline set. Intensity measurements that deviate from a corresponding intensity value of the baseline set by less than a specified threshold may be identified as calibration projection data.

As an example, a baseline calibration procedure may be performed at a manufacturing facility of the radiation system. During the baseline calibration procedure few, if any, objects may be positioned within the examination region (e.g., support rails, such as 112 in FIG. 1, are not present in the examination region). Accordingly, the detector array may be substantially uniformly exposed to radiation (e.g., similar to a conventional air calibration procedure). Based upon this baseline calibration procedure, a baseline set of intensity values may be determined that described the intensity(ies) that are expected to be measured by respective detector cells. This baseline set of intensity values may be compared, by the projection separation component 302, to intensity measurements of a projection and/or set of projections acquired during a subsequent calibration procedure, during which the detector array is partially shadowed by an object, to identify calibration projection data of the projection. In this way, calibration projection data may be separated from object projection data of the projection and/or set of projections using a baseline set of intensity values derived when the object(s) was not present in the examination region.

It may be appreciated that due to normal operation of the detector array, the intensity of radiation that is measured by a detector cell may change over time even when a same amount/energy of radiation is applied to the detector cell. For example, the detector cell may become less sensitive to radiation over time. Accordingly, in some embodiments, the baseline set of intensity values are updated by the projection separation component 302 prior to a comparison with intensity measurements acquired during a subsequent calibration procedure. In this way, one or more expected intensity values are altered (e.g., to take into consideration degradation of the detector cells and/or readout electronics).

As an example, in one embodiment, the projection separation component 302 is configured to compute an average intensity of a projection and/or set of projections acquired during the subsequent calibration procedure, and to compare this average intensity to an average intensity of the baseline set of intensity values to determine a degree of difference (e.g., where the degree of difference may be attributable to a decrease in detector cell sensitivity). Based upon this degree of difference, the baseline set of intensity values may be updated (e.g., such that the average intensity of the baseline set is substantially equal to the average intensity of the projection and/or set of projections). By way of example, the projection separation component 302 may determine that the average intensity of the baseline set is 2% higher than the average intensity of the projection and/or set of projections. Accordingly, respective intensity values of the baseline set may be reduced by 2% to generate an average intensity that is substantially equal to the average intensity of the projection and/or set of projections. Respective intensity values of the updated baseline set may then be compared to a corresponding intensity of the projection and/or set of projections to determine whether respective measurements are indicative of radiation traversing an object or not traversing an object.

The gain computation component 304 is configured to compute one or more gain corrections as a function of the calibration projection data. In one embodiment, the gain computation component 304 may compute a plurality of gain corrections for respective detector cells. In another embodiment, the gain computation component 304 may be configured to compute a single gain correction for respective detector cells. In yet another embodiment, the gain computation component 304 may be configured to compute one or more gain corrections for respective groups of two or more detector cells, for example. Whether multiple gain corrections are computed for a single detector cell, a single gain correction is computed for a detector cell, or a gain correction is computed for a group of detector cells may be a function of what is defined to be the correction unit.

The gain correction(s) is configured to substantially equalize the measurements when a uniform amount of radiation is applied to the detector array. Thus, the gain computation component 304 is configured to determine one or more gain correction(s) that cause the measurements of the calibration projection data to be substantially equal.

As an example, in some embodiments, an average intensity of the calibration projection data is computed. The average intensity may be compared, by the gain computation component 304, to calibration projection data yielded from a particular correction unit to compute a gain correction for the particular correction unit. For example, the average intensity measurement may be compared to a first measurement or first set of measurements of the calibration projection data and yielded from a first detector cell to compute a gain correction for the first detector cell. Likewise, the average intensity measurement may be compared to a second measurement or second set of measurements of the calibration projection data and yielded from a second detector cell to compute a gain correction for the second detector cell. In this way, a gain correction for respective detector cells may be computed that equalizes the detector cells (e.g., such that when the detector array is uniformly exposed to radiation, corrected data is indicative of substantially uniform measurements). Such a process may be repeated until a gain correction is computed for each of a plurality of detector cells.

It may be appreciated that due to the shadowing of the detector array during the calibration procedure, the calibration projection data from which the gain correction(s) are computed may not be complete. That is, a portion of the projection representative of the object may not be considered when computing the gain correction(s) and thus for some rotational angles, the measurements yielded from some detector cells may not be considered when computing the gain correction(s). Accordingly, in some embodiments, for a particular angular range (e.g., a particular range of view angles), the gain computation component 304 may not be able to compute a gain correction for a detector cell and/or a group of detector cells.

In embodiments where insufficient calibration projection data exists from which to compute a gain correction for a particular correction unit, the gain computation component 304 may be configured to compute a gain correction for the correction unit as a function of the computed gain correction for one or more neighboring correction units. By way of example, for a particular detector cell, there may be sufficient calibration projection data from which to compute a first gain correction to apply to measurements corresponding to a first set of views (e.g., views 0-120 in FIG. 2) and to compute a second gain correction to apply to measurements corresponding to a second set of views (e.g., views 241-360 in FIG. 2). However, there may be insufficient calibration correction data from which to compute a third gain correction to apply to measurements corresponding to a third set of views (e.g., views 121-240 in FIG. 2). Accordingly, in some embodiments, the gain computation component 304 is configured to compute the third gain correction based upon the first gain correction and the second gain correction (e.g., by averaging the first and second gain corrections, by interpolation, extrapolation, etc.). In other embodiments, the gain computation component 304 may be configured to determine the third gain correction as a function of the baseline set of intensity values and/or an updated baseline set of intensity values (e.g., where the gain computation component 304 computes the third gain correction with the assumption that the detector cell measured the intensity specified in the baseline set and/or the updated baseline set).

The gain correction(s) computed by the gain computation component 304 are output to a data storage unit (e.g., 128 in FIG. 1) configured to store the one or more gain corrections computed by the gain computation component 304. By way of example, in some embodiments, the gain computation component 304 is configured to arrange the gain corrections into an air table, and the air table is stored in the data storage unit for later retrieval by the data correction component 300 when an examination procedure is performed. Although the instant embodiment illustrates the data storage unit as being separate from the data correction component 300, in another embodiment, the data storage unit, may be located within the data correction component 300.

The data correction component 300 further comprises a gain correction component 306 configured to correct measurements of a projection(s) acquired from an examination procedure and representative of a subject under examination. By way of example, in one embodiment, the gain correction component 306 is operably coupled to the data storage unit and is configured to retrieve one or more gain corrections from the data storage unit when a projection(s) indicative of a subject is acquired from an examination procedure. The gain correction component 306 is further configured to apply respective gain corrections to corresponding measurements represented in the projection(s) to correct the measurements. In this way, the projection(s) yielded from the examination procedure are adjusted as a function of one or more gain corrections computed from calibration projection data yielded from a calibration scan.

In some embodiments, it may be desirable to relocate, during the calibration procedure, one or more objects that shadow the detector array. For example, in one embodiment, a radiation system comprises an object translation component (not shown) that is configured to locate an object in a first position relative to the axis of rotation for a first rotation of the calibration procedure and to relocate the object to a second position relative to the axis of rotation for a second rotation of the calibration procedure. The relocation of the object from a first position to a second position during the calibration procedure may cause the object to be represented differently in a first projection, acquired when the object was located at the first position, relative to the representation of the object in a second projection, acquired when the object was located at the second position.

Figure 5:
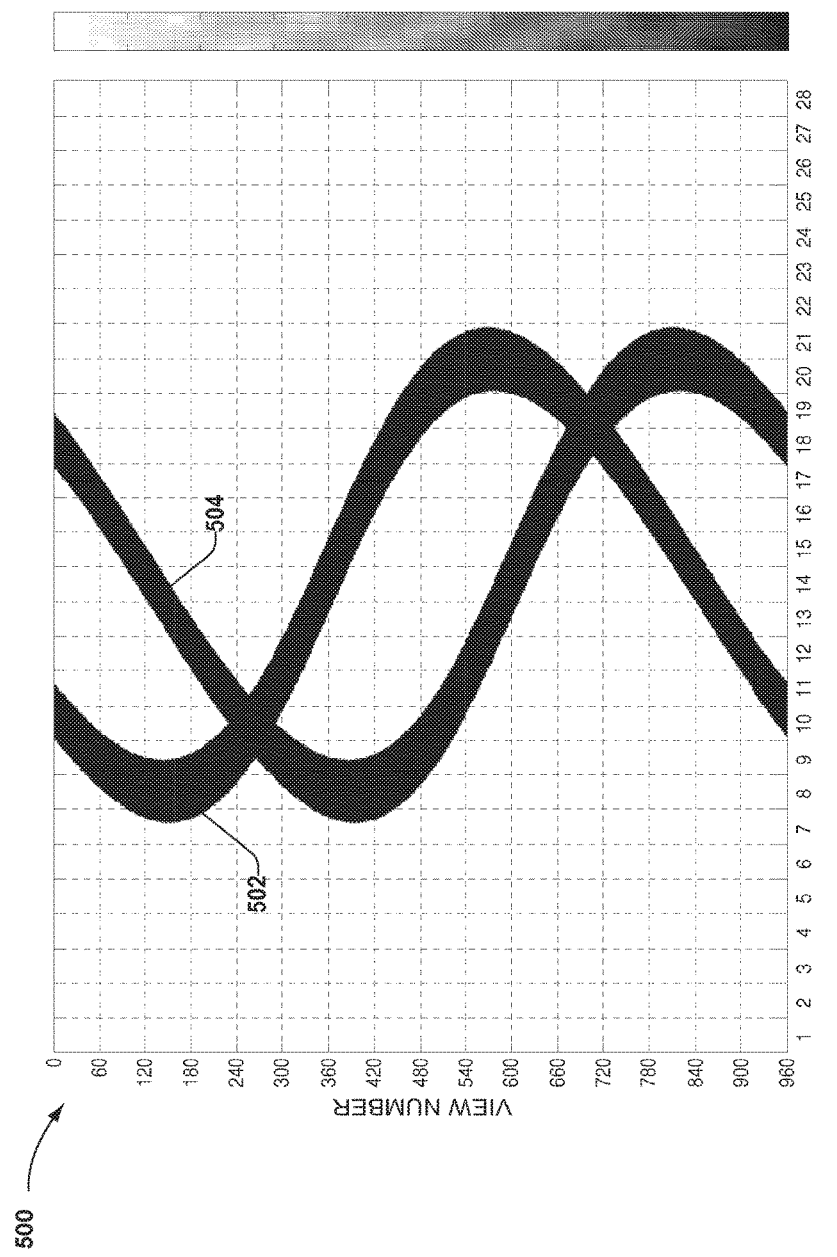
FIG. 5 illustrates an example projection set yielded from a calibration procedure.

By way of example, with reference to FIG. 5, a second example projection set 500 is illustrated. A first sinusoid 502 is representative of a first object that is shadowing a detector array, and a second sinusoid 504 is representative of a second object that is shadowing the detector array. The first object is the same object as represented by the first sinusoid 202 of the projection set 200 in FIG. 2, and the second object is the same object as represented by the second sinusoid 204 of the projection set 200 in FIG. 2. The changes in the shape of the sinusoids 502, 504 of the second projection set 500 relative to the sinusoids 202, 204 of the first projection set 200 is due to, among other things, the relocation of the first object and the second object relative to an axis of rotation for the rotating gantry, detector array, and/or radiation source (e.g., support rails for a gurney initially in a lowered position and then relocated into a raised position). That is, the first projection set 200 was acquired when the objects were a first distance away from the axis of rotation and the second projection set 500 was acquired when the objects were a second distance away from the axis of rotation, causing the projection sets 200, 500 to appear differently even though the two projection sets 200, 500 are representative of the same objects and acquired during a same calibration procedure.

It may be appreciated that a comparison between the first projection set 200 and the second projection set 500 may reveal that, for a given view, the detector cells that are shadowed (e.g., and thus correspond to the blackened areas of the projection sets 200, 500) may differ between projection sets 200, 500. Accordingly, for a given view number, a first detector cell may be shadowed when the first projection set 200 is acquired and may not be shadowed when the second projection set 500 is acquired. Thus, the use of two or more projection sets, representing an object(s) at various positions relative to the axis of rotation, may facilitate acquiring additional calibration correction data that may be useful to compute one or more gain corrections. For example, calibration projection data from the second projection set 500 may be used to fill in portions of the first projection set 200 that comprise object projection data (e.g., to derive a projection set that represents little, if any, of the object(s) that shadowed the detector array).

Figure 4:
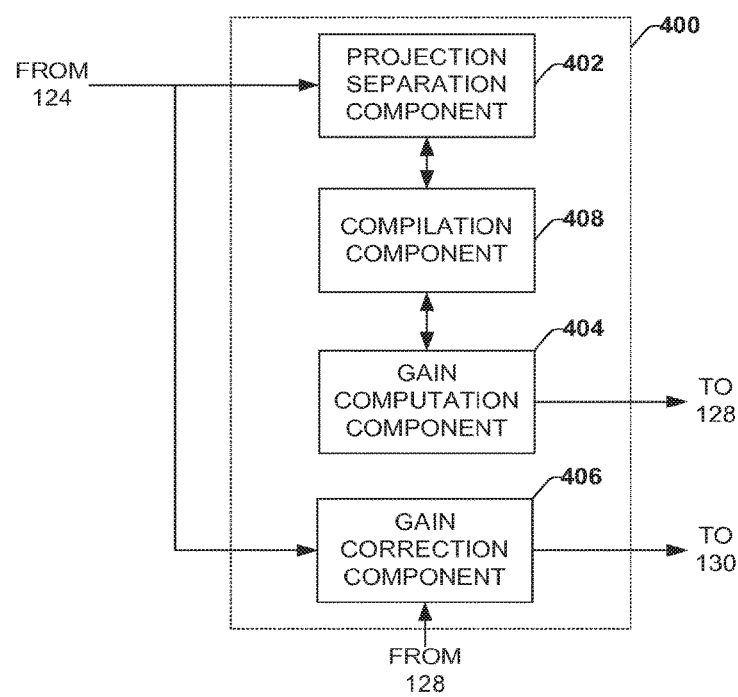
FIG. 4 is a schematic block diagram illustrating an example data correction component.

Referring to FIG. 4, an example data correction component 400 is illustrated that may be configured to compute one or more gain corrections when an object has been relocated during a calibration procedure and a plurality of projection sets have been acquired (e.g., respectively representative of the object at a different position relative to the axis of rotation). Like the data correction component 300 of FIG. 3, the data correction component 400 of FIG. 4 comprises a projection separation component 402 (e.g., 302 in FIG. 3), a gain computation component 404 (e.g., 304 in FIG. 3), and a gain correction component 406 (e.g., 306 in FIG. 3). Accordingly, for purposes of brevity, features and/or functions of such components may not be described with respect to the data correction component 400 of FIG. 4.

The data correction component 400 further comprises a compilation component 408 that is not present in the data correction component 300 of FIG. 3. The compilation component 408 is configured to compile calibration projection data from a first projection set, representative of the object being positioned in a first position relative to the axis of rotation (e.g., gurney support rails lowered), with calibration projection data from a second projection set, representative of the object being positioned in a second position relative to the axis of rotation (e.g., gurney support rails raised). In this way, compiled calibration projection data may be generated that provides additional information from which one or more gain corrections can be computed (e.g., relative to the information derived from calibration projection data of a single projection set).

When two or more projection sets are generated during a calibration procedure, the projection separation component 402 may be configured to separate the calibration projection data of respective projection sets from the object projection data of respective projection sets. For example, the projection separation component 402 may be configured to separate first calibration projection data of a first projection set from first object projection data of the first projection set, second calibration projection data of a second projection set from second object projection data of the second projection set, etc.

The compilation component 408 is configured to combine the calibration projection data of respective projection sets to yield compiled calibration projection data. For example, the compilation component 408 may combine the first calibration projection data with the second calibration projection data to generate compiled calibration projection data. By combining the first calibration projection data with the second calibration projection data, a combined projection set may be derived, where the combined projection set represents less of the object(s) than either of the first projection set or the second projection set. By way of example, in the combined projection set, at least some of the object projection data of the first projection set may be substituted with corresponding calibration projection data of the second projection set (e.g., yielded from a same set of detector cells at a same view number(s)).

In embodiments where a first portion of the first projection set comprises first calibration projection data and a corresponding first portion of the second projection set (e.g., yielded from a same set of detector cells at a same view number(s)) comprises second calibration projection data, the first calibration projection data and the second calibration projection data may be combined (e.g., averaged) and/or at least some of the first calibration projection data and/or second calibration projection data may be discarded. For example, a rule may be devised that provides that the compilation component 408 is to discard the second calibration projection data when the first projection set comprises corresponding calibration projection data (e.g., indicative of measurements from a same set of detector cells during a same view number(s)).

Where the data correction component 400 is configured to generate compiled calibration projection data, the gain computation component 404 may be configured to compute one or more gain corrections as a function of the compiled calibration projection data. In this way, the one or more gain corrections may be computed as a function of a plurality of projection sets, as opposed to merely one projection set as described with respect to FIG. 2.

Figure 6:
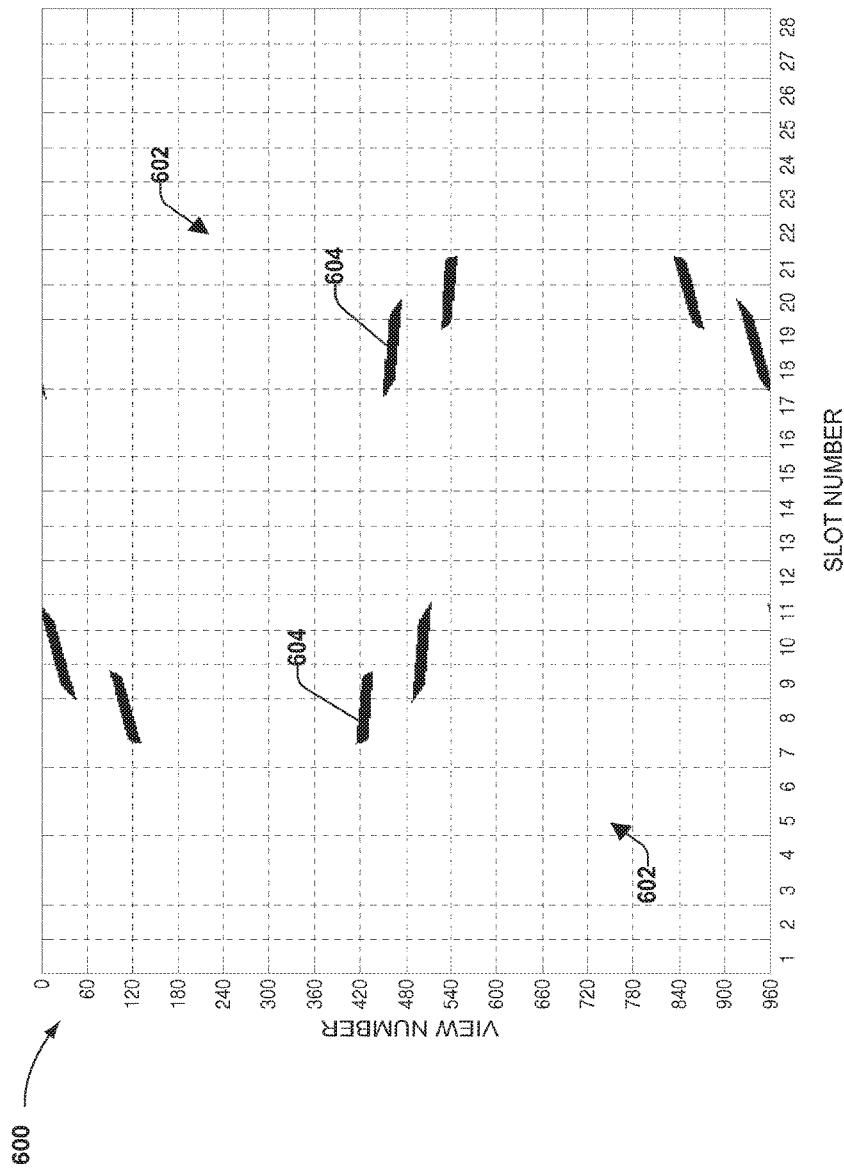
FIG. 6 illustrates an example projection set yielded from compiling first calibration projection data of a first projection set with second calibration projection data of a second projection set.

FIG. 6 illustrates an example projection set 600 that may be derived by combining the calibration projection data from a first projection set (e.g., 200 in FIG. 2) with the calibration projection data from a second projection set (e.g., 500 in FIG. 5), such as by a compilation component (e.g., 408 in FIG. 4). The white portions 602 of the projection set 600 represents calibration projection data that was identified in at least one of the first projection set or the second projection set and was utilized to generate compiled calibration projection data. The darker portions 604 of the projection set 600 represent areas where no calibration projection data was identified in either of the first projection set or the second projection set. Accordingly, the darker portions represent measurements from detector cells that were shadowed during both a first rotation from which the first projection set was generated and a second rotation from which the second projection set was generated.

It may be appreciated that by combining first calibration projection data of first projection set with second calibration projection data of the second projection set, there may be fewer instances where there are no measurements indicative of radiation that did not traverse an object(s). That is, a smaller percentage of the projection set 600 illustrated in FIG. 6 is darkened compared to the first projection set 200 of FIG. 2 and compared to the second projection set 500 of FIG. 5. Accordingly, there is more data from which to compute gain corrections, for example.

Figure 7:
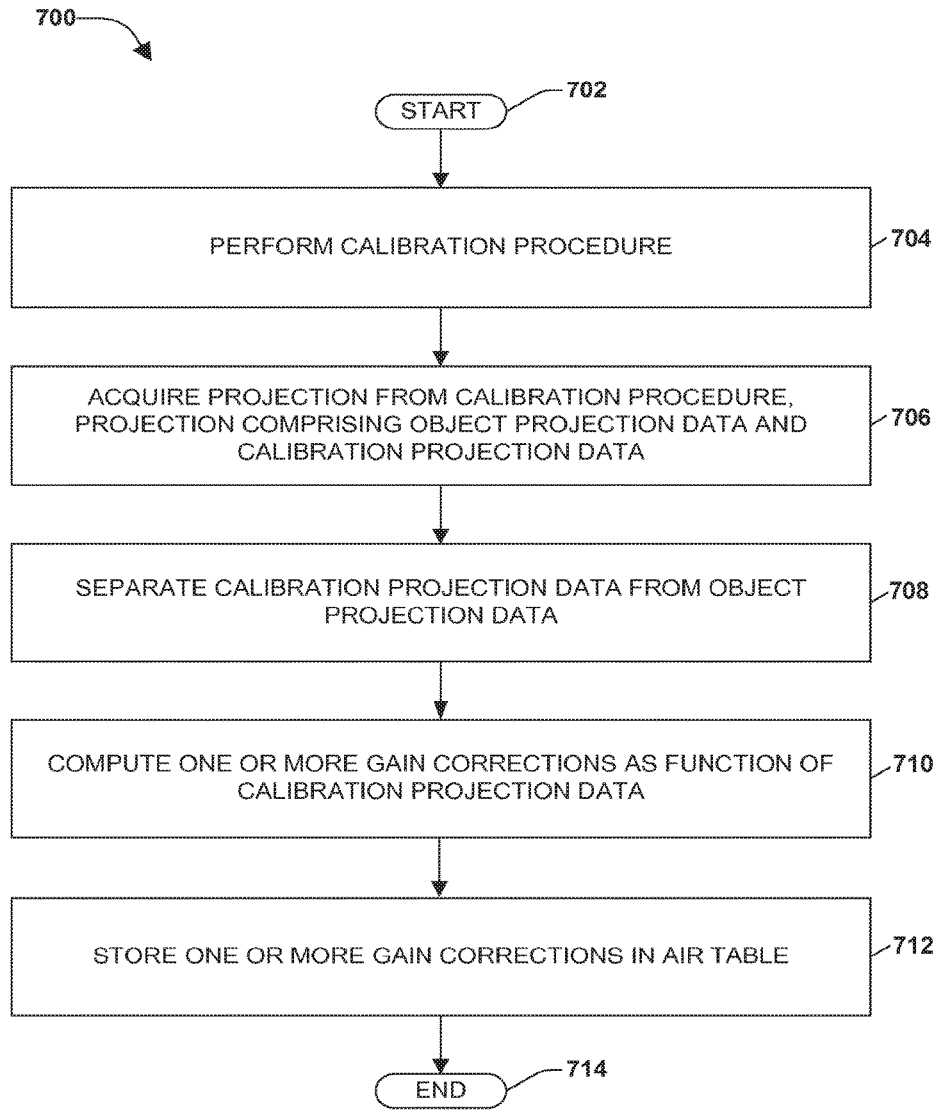
FIG. 7 is a flow chart diagram of an example method for calibrating a computed tomography (CT) system when a field of view is partially obstructed by an object.

FIG. 7 illustrates an example method 700 for calibrating a computed tomography (CT) system, such as when a field of view is partially obstructed by an object and/or a detector array of the CT system is at least partially masked by the object. It may be appreciated that for purposes of brevity, actions and/or features described above may not be further described in detail with respect to the example method 700, but may find applicability to such a method 700.

The example method 700 begins at 702, and a calibration procedure is performed at 704. The calibration procedure comprises emitting radiation from a radiation source of the CT system toward a detector array of the CT system while an object of the CT system is comprised in an examination region of the CT system. Accordingly, the field of view may be obstructed by the object such that the detector array is at least partially shadowed from the perspective of the radiation source (e.g., a portion of the detector array is hidden behind the object). Moreover, due to the obstruction of the object, in some embodiments, the calibration procedure may comprise non-uniformly exposing the detector array to radiation (e.g., due to radiation that traverses the object being attenuated differently than radiation that did not traverse the object).

In some embodiments, the calibration procedure is performed while the detector array and the radiation source are substantially fixed relative to the object. In other embodiments, the calibration procedure may comprise rotating at least one of the radiation source and/or detector array relative to the object during the calibration procedure to view the object at multiple view angles. That is, stated differently, in some embodiments, the radiation source and/or detector array may rotate about an axis of rotation causing the perspective of the object to change from the viewpoint of at least one of the radiation source and/or detector array.

The calibration procedure is configured to generate one or more projections indicative of measurements acquired by the detector array, or rather detector cells of the detector array during a particular measurement interval (e.g., which may correlate with the rotation of the radiation source and/or detector array). For example, in an embodiment, a first set of one or more projections is generated that is indicative of measurements acquired during a first 360 degree rotation of the radiation source and detector array, and a second set of one or more projections is generated that is indicative of measurements acquired during a second 360 degree rotation of the radiation source and detector array (e.g., where a single projection of a set may be indicative of measurements acquired during merely a portion the 360 degree rotation, such as 1 degree of the rotation or less).

At 706 in the example method 700, at least one of the generated projections is acquired, such as by a data correction component (e.g., 126 in FIG. 1) of the CT system. At least some of the projections acquired from a calibration procedure performed while the field of view is partially obstructed by an object comprise object projection data indicative of radiation the traversed the object and calibration projection data indicative of radiation that did not traverse the object. For example, the first set of one or more projections yielded from the calibration procedure may comprise first object projection data and first calibration projection data and the second set of one or more projections yielded from the calibration procedure may comprise second object projection data and second calibration projection data.

At 708 in the example method 700, the calibration projection data of at least one projection is separated from the object projection data of the projection. By way of example, first calibration projection data of a first projection may be separated from first object projection data of the first projection, second calibration projection data of a second projection maybe separated from second object projection data of the second projection, etc.

It may be appreciated that numerous techniques are contemplated for identifying calibration projection data of a projection and/or for separating the calibration projection data of a projection from object projection data of the projection. By way of example, in one embodiment, the separating comprises averaging an intensity of radiation measured by one or more detector cells (e.g., where measurements of the projection may be indicative of intensity) to determine an average intensity for the projection and/or a set of projections and comparing the average intensity of the projection and/or set of projections to respective intensity measurements of the projection and/or set of projections to determine measurements representative of radiation that did not traverse the object (e.g., thus identifying measurements indicative of calibration projection data). As an example, intensity measurements that deviate from the average intensity by less than a specified threshold may be identified as calibration projection data.

In another embodiment, the separating comprises identifying instances where a detector cell was not shadowed by an object and separating measurements acquired from the detector cell when it was not shadowed by the object from measurements acquired from the detector cell when it was shadowed by the object. By way of example, a light source may be positioned adjacent the radiation source and may be configured to cast a shadow over portions of the detector array that are obstructed by the object. A sensor may be positioned to identify areas of the detector array that are shadowed from the light and/or to identify areas of the detector array that are not shadowed from the light. Measurements yielded from areas of the detector array that are shadowed from the light may be labeled as object projection data, and measurements yielded from areas of the detector array that are not shadowed from the light may be labeled as calibration projection data.

In yet another embodiment, the separating may comprise determining one or more expected intensity measurements of respective detector cells of a detector array, such as based upon an initial calibration procedure (e.g., performed when few to no objects are present in the examination region), to generate a baseline set of measurements, such as a baseline set of intensity values. Such baseline measurements may be compared to corresponding measurements acquired during the calibration procedure performed at 704. Measurements acquired during the calibration procedure that are within a specified deviation of a corresponding baseline measurement may be labeled as calibration projection data and measurements that are not within the specified deviation of a corresponding baseline measurement may be labeled as object projection data, for example.

It is to be appreciated that the foregoing separation techniques are provided merely as example and are not intended to limit the scope of the application, including the scope of the claims.

At 710 in the example method 700, one or more gain corrections are computed as a function of the calibration projection data of the projection(s) and/or as a function of one or more projections generated from a detector array that is non-uniformly exposed to radiation. The one or more gain corrections are configured to correct (e.g., to some extent) one or more measurements yielded from a detector array of a CT system during an examination of a subject. That is, stated differently, the one or more gain corrections are configured to correct a projection(s) representative of a subject undergoing and/or that underwent an examination.

Numerous techniques for computing a gain correction from calibration projection data (e.g., indicative of radiation merely traversing air) are contemplated to compute the one or more gain corrections at 710. By way of example, in some embodiments, an average intensity of measurements included in the calibration projection data is determined, and respective measurements included in the calibration projection are compared to the average intensity. For respective measurements, a gain correction may be determined that adjusts the measurement to make the measurement substantially equal to the average intensity. In other embodiments, a group of measurements included in the calibration projection data and yielded from a same detector cell are averaged, and the average is compared to an average intensity to determine a gain correction for the detector cell.

It may be appreciated that where a plurality of projections or a plurality of sets of projections are generated, prior to computing the one or more gain corrections at 710, the calibration projection data of respective projections or sets of projections may be compiled to generate compiled calibration projection data. For example, first calibration projection data of a first projection set may be compiled with second calibration data of a second projection set acquired during a same calibration procedure to generate compiled calibration projection data, and the one or more gain corrections may be computed as a function of the compiled projection data.

As described with respect to FIGS. 2, 5, and 6, in some embodiments, an object may be repositioned or relocated within the examination region between a time when a first projection set (e.g., indicative of a first scan of the object) is generated and a time when a second projection set (e.g., indicative of a second scan of the object) is generated. In this way, the first projection set may comprise calibration projection data pertaining to portions of an examination that is not comprised in calibration projection data of the second projection set and/or vice-versa.

At 712 in the example method 700, the one or more gain corrections computed at 710 are stored in an air table for use when correcting projections generated from an examination of a subject and at least partially representative of the subject.

Figure 8:
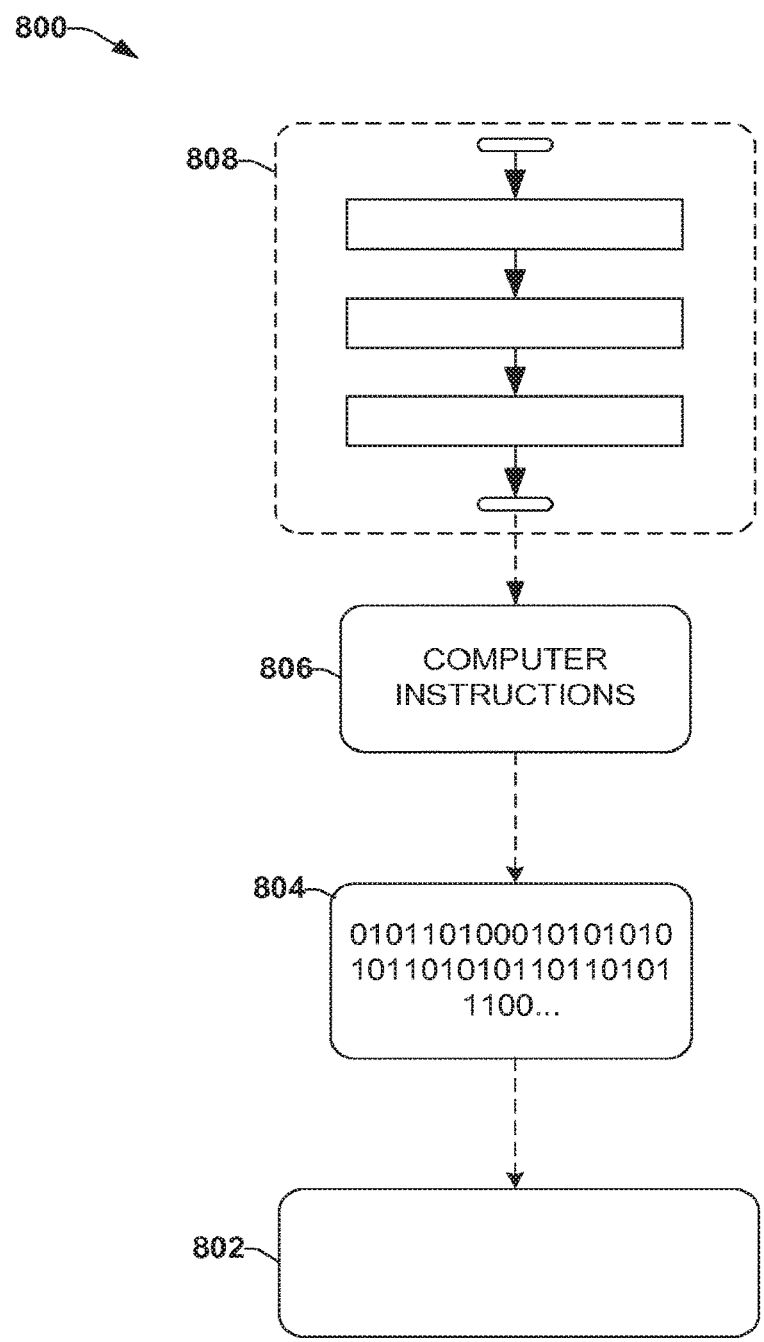
FIG. 8 is an illustration of an example computer-readable medium comprising processor-executable instructions wherein one or more of the provisions set forth herein may be embodied.

The example method 700 ends at 714. Still another embodiment involves a computer-readable medium comprising processor-executable instructions configured to implement one or more of the techniques presented herein. An example computer-readable medium (e.g., memory) that may be devised in these ways is illustrated in FIG. 8, wherein the implementation 800 comprises a computer-readable medium 802 (e.g., a flash drive, CD-R, DVD-R, application-specific integrated circuit (ASIC), field-programmable gate array (FPGA), a platter of a hard disk drive, etc.), on which is encoded computer-readable data 804. This computer-readable data 804 in turn comprises a set of processor-executable instructions 806 that when executed via a processing unit(s) is configured to operate according to one or more of the principles set forth herein. In some embodiments, the processor-executable instructions 806 may be configured to perform a method 808, such as at least some of the example method 700 of FIG. 7, for example. In other embodiments, the processor-executable instructions 806 may be configured to implement a system, such as at least some of the exemplary environment 100 of FIG. 1, the exemplary data correction component 300 of FIG. 3, and/or the exemplary data correction component 400 of FIG. 4, for example. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this disclosure, "or" is intended to mean an inclusive "or" rather than an exclusive "or." In addition, "a" and "an" as used in this disclosure are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used in either the detailed description or the claims, such terms are intended to be inclusive in a manner similar to the term "comprising."

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this disclosure, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc., for features, elements, items, etc. (e.g., "a first channel and a second channel" generally corresponds to "channel A and channel B," where channel A and channel B may be two different channels, two identical channels, or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. A method of calibrating a computed tomography (CT) system when a field of view is partially obstructed by an object, comprising:
  acquiring a projection, corresponding to a first view angle of a CT scan, from a calibration procedure performed while the field of view is partially obstructed by the object, the projection comprising object projection data indicative of radiation that traversed the object and calibration projection data indicative of radiation that did not traverse the object;
  separating the calibration projection data from the object projection data, the separating comprising:
    comparing the projection to a second projection, corresponding to the first view angle, acquired while the field of view was not partially obstructed by the object to identify the calibration projection data; and
  computing one or more gain corrections as a function of the calibration projection data, the one or more gain corrections utilized during an examination procedure to correct measurements yielded from a detector array of the CT system.

2. The method of claim 1, comprising adjusting one or more values within the second projection prior to the comparing.

3. The method of claim 2, the adjusting comprising:
adjusting the one or more values based upon a length of time that has occurred between the second projection and the projection.

4. The method of claim 2, the adjusting comprising:
averaging measurements of the projection acquired from a plurality of detector cells to determine an average measurement for the projection; and
adjusting the one or more values based upon the average measurement for the projection.

5. The method of claim 1, comprising:
acquiring a second projection, corresponding to a second view angle of the CT scan, from the calibration procedure, the second projection comprising second object projection data indicative of radiation that traversed the object and second calibration projection data indicative of radiation that did not traverse the object;
separating the second calibration projection data from the second object projection data; and
compiling the calibration projection data of the projection with the second calibration projection data of the second projection to generate compiled calibration projection data, wherein the computing comprises:
computing the one or more gain corrections as a function of the compiled calibration projection data.

6. A computed tomography (CT) system, comprising:
a radiation source configured to emit radiation;
a detector array comprising a plurality of detector cells configured to detect at least some of the radiation;
a projection separation component configured to:
acquire a projection, corresponding to a first view angle of a CT scan, from a calibration procedure performed while a field of view between the radiation source and the detector array is partially obstructed by an object; and
compare the projection to a second projection, corresponding to the first view angle, acquired while the field of view was not partially obstructed by the object to identify calibration projection data; and
a gain computation component configured to compute one or more gain corrections using the calibration projection data to apply to measurements yielded from an examination of a subject.

7. The system of claim 6, wherein the projection separation component is configured to compare intensity measurements acquired during a calibration procedure to a baseline intensity value.

8. The system of claim 6, further comprising a compilation component configured to compile the calibration projection data of the projection with second calibration projection data of a second projection to generate compiled calibration projection data.

9. The system of claim 8, wherein the projection is representative of measurements acquired during a first rotation of at least one of the detector array or the radiation source relative to the object and the second projection is representative of measurements acquired during a second rotation.

10. The system of claim 6, further comprising an object translation component configured to move the object relative to an axis of rotation for at least one of the detector array or the radiation source during the calibration procedure.

11. The system of claim 10, wherein the object translation component is configured to locate the object in a first position relative to the axis of rotation during a first rotation from which measurements represented in the projection are acquired and to locate the object in a second position relative to the axis of rotation during a second rotation from which measurements represented in a second projection, corresponding to a first view angle of the CT scan, are acquired.

12. The system of claim 6, further comprising:
a compilation component configured to compile the calibration projection data of the projection with second calibration projection data of a second projection to generate compiled calibration projection data, and
the gain computation component configured to compute the one or more gain corrections as a function of the compiled calibration projection data.

* * * * *